US012207799B2

United States Patent
Govari et al.

(10) Patent No.: US 12,207,799 B2
(45) Date of Patent: Jan. 28, 2025

(54) HIGHLY BENDABLE CAMERA FOR EYE SURGERY

(71) Applicant: JOHNSON & JOHNSON SURGICAL VISION, INC., Santa Ana, CA (US)

(72) Inventors: Assaf Govari, Haifa (IL); Vadim Gliner, Binyamina (IL); Ilya Sitnitsky, Nahariya (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 272 days.

(21) Appl. No.: 17/135,882

(22) Filed: Dec. 28, 2020

(65) Prior Publication Data

US 2022/0202286 A1    Jun. 30, 2022

(51) Int. Cl.
*A61B 1/313* (2006.01)
*A61B 1/005* (2006.01)
(Continued)

(52) U.S. Cl.
CPC ............ *A61B 1/313* (2013.01); *A61B 1/0052* (2013.01); *A61B 1/0056* (2013.01); *A61B 1/0057* (2013.01); *A61B 1/05* (2013.01); *A61B 1/07* (2013.01); *A61B 5/062* (2013.01); *A61F 9/007* (2013.01)

(58) Field of Classification Search
CPC ........... A61B 1/313; A61B 1/05; A61B 5/062; A61B 1/0056; A61F 9/007
See application file for complete search history.

(56) References Cited

U.S. PATENT DOCUMENTS

| 4,607,622 A | 8/1986 | Fritch et al. |
| 5,106,381 A * | 4/1992 | Chikama ........... A61M 25/0147 604/528 |

(Continued)

FOREIGN PATENT DOCUMENTS

| CN | 105640698 A | 6/2016 |
| EP | 0513224 B1 | 10/1996 |
| WO | 2020222238 A1 | 11/2020 |

OTHER PUBLICATIONS

Ajlan R.S., et al., "Endoscopic Vitreoretinal Surgery: Principles, Applications and New Directions," International Journal of Retina and Vitreous, Jun. 2019, 5 (15), 11 pages.

(Continued)

*Primary Examiner* — Anh Tuan T Nguyen
*Assistant Examiner* — Rynae E Boler (57) ABSTRACT

Apparatus, including a tube having proximal and distal ends and an internal lumen. The distal end may bend up to 270°, and the tube may be inserted into an eye. A planar resilient strip, having proximal and distal ends, is inserted into the internal lumen, and the strip distal end is fixed to the tube distal end. A coil spring is fixed to the strip proximal end so that a coil spring symmetry axis is coplanar with the strip. A camera, mounted with the strip distal end, images the eye interior. A wire is fixed to the strip distal end, so that a predetermined force on the wire causes the tube distal end to bend by a preset angle. A magnetometer at the tube proximal end is configured, when a nonvarying magnetic field traverses it, to provide a signal that, when taken with the preset angle, indicates a camera orientation.

13 Claims, 8 Drawing Sheets

(51) Int. Cl.
    *A61B 1/05* (2006.01)
    *A61B 1/07* (2006.01)
    *A61B 5/06* (2006.01)
    *A61F 9/007* (2006.01)

(56) References Cited

U.S. PATENT DOCUMENTS

| | | | |
|---|---|---|---|
| 5,255,668 A * | 10/1993 | Umeda | A61M 25/0147 604/528 |
| 5,391,199 A | 2/1995 | Ben-Haim | |
| 5,443,489 A | 8/1995 | Ben-Haim | |
| 5,558,091 A | 9/1996 | Acker et al. | |
| 5,820,591 A * | 10/1998 | Thompson | A61M 25/0136 604/95.01 |
| 5,855,560 A * | 1/1999 | Idaomi | A61M 25/0136 604/528 |
| 6,172,499 B1 | 1/2001 | Ashe | |
| 6,177,792 B1 | 1/2001 | Govari et al. | |
| 6,788,967 B2 | 9/2004 | Ben-Haim et al. | |
| 7,083,591 B2 | 8/2006 | Cionni | |
| 7,186,258 B2 | 3/2007 | Sabet | |
| 7,563,242 B2 | 7/2009 | Yaguchi et al. | |
| 7,841,503 B2 | 11/2010 | Sonnenschein | |
| 8,016,843 B2 | 9/2011 | Escaf | |
| 8,398,587 B2 | 3/2013 | Dewaele et al. | |
| 8,403,828 B2 | 3/2013 | Mawn et al. | |
| 8,708,488 B2 | 4/2014 | Kraus et al. | |
| 9,364,982 B2 | 6/2016 | Schaller | |
| 9,463,081 B2 | 10/2016 | Urakabe | |
| 9,498,377 B2 | 11/2016 | McCary et al. | |
| 9,962,226 B2 | 5/2018 | Brennan et al. | |
| 10,524,822 B2 | 1/2020 | Aljuri et al. | |
| 10,561,822 B2 | 2/2020 | Wang | |
| 10,624,784 B2 | 4/2020 | Saimovici | |
| 2001/0010003 A1 | 7/2001 | Lai | |
| 2003/0191369 A1 | 10/2003 | Arai et al. | |
| 2005/0054900 A1 * | 3/2005 | Mawn | A61B 5/064 600/156 |
| 2005/0288627 A1 * | 12/2005 | Mogul | A61M 25/0136 604/95.04 |
| 2008/0058708 A1 | 3/2008 | Akahoshi | |
| 2009/0326326 A1 * | 12/2009 | Lin | A61B 1/00071 600/146 |
| 2012/0022546 A1 | 1/2012 | Hubschman et al. | |
| 2012/0035467 A1 | 2/2012 | Lichtenstein | |
| 2012/0089014 A1 | 4/2012 | Sabczynski et al. | |
| 2012/0223937 A1 | 9/2012 | Bendall | |
| 2013/0072917 A1 | 3/2013 | Kaschke et al. | |
| 2013/0077048 A1 | 3/2013 | Mirlay | |
| 2013/0102922 A1 | 4/2013 | Gooding et al. | |
| 2013/0317417 A1 | 11/2013 | Claus et al. | |
| 2014/0024969 A1 | 1/2014 | Govari et al. | |
| 2014/0320621 A1 | 10/2014 | Sonnenschein et al. | |
| 2014/0364870 A1 | 12/2014 | Alvarez et al. | |
| 2016/0030240 A1 | 2/2016 | Gonenc et al. | |
| 2016/0101263 A1 | 4/2016 | Blumenkranz et al. | |
| 2017/0164869 A1 * | 6/2017 | Lee | A61B 1/00147 |
| 2019/0000563 A1 | 1/2019 | Schneider et al. | |
| 2019/0004305 A1 * | 1/2019 | Duckett, III | A61B 1/00096 |
| 2019/0070395 A1 * | 3/2019 | Govari | A61M 25/09 |
| 2020/0107701 A1 | 4/2020 | Gliner et al. | |
| 2021/0093177 A1 | 4/2021 | Anderson et al. | |
| 2021/0145642 A1 | 5/2021 | Berlin | |
| 2021/0169695 A1 | 6/2021 | Gliner et al. | |
| 2022/0007937 A1 | 1/2022 | Govari et al. | |
| 2022/0257416 A1 * | 8/2022 | Foulkes | A61F 9/00781 |

OTHER PUBLICATIONS

Yu Y.Z., et al., "Endoscopy-assisted Vitrectomy in the Anterior Vitreous," International Journal of Ophthalmology, 2018, vol. 11 (3), pp. 506-511.

Francis et al., 2014, Endoscopic ophthalmic surgery of the anterior segment, Survey of Ophthalmology, vol. 59, Issue 2.

Cheng et al., vol. 10, Supplement 6 (Apr. 2018): Journal of Thoracic Disease [Asia Thoracic Cancer Care Summit 2018 (Part I)] / Innovative surgical endoscopes in video-assisted thoracic surgery.

Endoeye Flex 3D (LTF-190-10-3D) | Olympus America | Medical, https://medical.olympusamerica.com/products/laparoscopes/endoeye-flex-3d.

\* cited by examiner

HIGHLY BENDABLE CAMERA FOR EYE SURGERY

FIELD OF THE INVENTION

This invention relates generally to eye surgery, and specifically to inspection of the results of the surgery.

BACKGROUND OF THE INVENTION

Typically during eye surgery a surgeon may observe the procedure directly through the pupil of the eye being operated on. In addition to direct observation, the surgeon may use an imaging device to observe the procedure. Some imaging devices known in the art are briefly summarized below.

U.S. Pat. No. 4,607,622, to Fritch, et al., describes an ocular endoscope which is stated to be designed primarily for use in treating, diagnosing and investigating problems associated with the eye.

U.S. Pat. No. 8,403,828, to Mawn, et al., describes a flexible endoscope for ophthalmic orbital surgery. The endoscope is stated to include an image fiber that communicates image information from the distal end of a flexible probe comprised in the endoscope.

U.S. Pat. No. 7,841,503, to Sonnenschein, et al., describes an endoscopic device comprising linear staplers and a video camera on the distal end of the device.

U.S. Pat. No. 8,398,587, to Dewaele, et al., describes a steerable tube. It is stated that for difficult-to-see and/or hard-to-reach places, a distal end of the tube may advantageously be provided with an endoscopic camera or lens, which may be implemented by fiber scope or chip-on-a-stick.

PCT Application WO2011,154,970A1, to Mirlay, describes an integrated fiber optic ophthalmic intraocular surgical device with a camera.

SUMMARY OF THE INVENTION

An embodiment of the present invention provides apparatus, including:
- a flexible biocompatible tube, having a proximal end, a distal end, and an internal lumen, wherein the distal end is configured to bend by up to 270°, and wherein the tube is configured to be inserted into an eye;
- a planar resilient strip, having a proximal end and a distal end, wherein the strip is inserted into the internal lumen, and wherein the distal end of the strip is fixed to the distal end of the tube;
- a coil spring, including a lumen, wherein the coil spring is fixed to the proximal end of the strip so that an axis of symmetry of the coil spring is coplanar with the strip;
- a camera, wherein the camera is mounted with the distal end of the strip, and wherein the camera is configured to image an internal portion of the eye;
- a wire, extending through the lumen of the coil and having a termination fixed to the distal end of the strip, so that a predetermined force on the wire causes the distal end of the tube to bend by a preset angle; and
- a magnetometer mounted with the internal lumen at the proximal end of the tube, and configured, in response to a nonvarying magnetic field traversing the magnetometer, to provide a signal that, when taken with the preset angle, is indicative of an orientation of the camera.

In a disclosed embodiment the apparatus includes a handle, connected to the proximal end of the tube, wherein the handle includes a control configured to apply the predetermined force on the wire.

In another disclosed embodiment the signal provided by the magnetometer includes a difference between an initial signal, generated when the orientation of the camera is in an initial orientation, and a subsequent signal, generated when the orientation of the camera is in a subsequent orientation different from the initial orientation.

In a further disclosed embodiment the coil spring includes a tension spring having coils contacting each other when the spring is unloaded.

In a yet further disclosed embodiment the apparatus includes at least one fiber optic located in the internal lumen and configured to provide illumination to the internal portion of the eye imaged by the camera.

There is further provided, according to an embodiment of the present invention, a method, including:
  providing an apparatus, consisting of:
    a flexible biocompatible tube having a proximal end, a distal end, an internal lumen, wherein the distal end is configured to bend by up to 270°; a magnetometer, wherein the magnetometer is coupled with the internal lumen at the proximal end of the tube, and wherein the magnetometer is configured to provide a signal indicative of an orientation of the magnetometer with respect to a nonvarying magnetic field traversing the magnetometer; and a camera, wherein the camera is coupled with the distal end of the tube;
  inserting the distal end of the tube into an eye;
  bending the distal end of the tube by a preset bending angle;
  rotating the proximal end of the tube about a symmetry axis of the proximal end, while activating the camera to acquire images of an internal portion of the eye;
  in response to the signal provided by the magnetometer, halting rotation of the proximal end when the rotation is 360°; and
  presenting the images acquired by the camera during the rotation on a screen.

In an alternative embodiment presenting the images includes stitching the images to form a coherent image of the internal portion of the eye.

In a further alternative embodiment the method includes performing an iteration of the steps of bending the distal end of the tube, rotating the proximal end of the tube, and halting rotation of the proximal end when the rotation is 360°, and wherein presenting the images comprises presenting the images acquired during the iteration. The method may also include halting the iteration when the internal portion of the eye has been completely imaged.

There is further provided, according to an embodiment of the present invention, apparatus, including:
- a flexible biocompatible tube, having a distal end and an internal lumen, wherein the distal end is configured to bend by up to 270°, and wherein the tube is configured to be inserted into an eye;
- a planar resilient strip, having a proximal end and a distal end, wherein the strip is inserted into the internal lumen, and the distal end of the strip is fixed to the distal end of the tube;
- a coil spring, including a coil lumen, wherein the coil spring is fixed to the proximal end of the strip so that an axis of symmetry of the coil spring is coplanar with the strip;

a camera, wherein the camera is mounted at the distal end of the strip, and wherein the camera is configured to image an internal portion of the eye;

a wire, extending through the coil lumen and having a termination fixed to the distal end of the strip, so that a force on the wire causes the distal end of the tube to bend; and a magnetic field sensor mounted with the distal end of the strip, and configured, in response to a magnetic field traversing the sensor, to provide a signal that is indicative of an orientation of the camera.

The present disclosure will be more fully understood from the following detailed description of the embodiments thereof, taken together with the drawings, in which:

DETAILED DESCRIPTION OF EMBODIMENTS

Overview

Phacoemulsification of a natural lens having a cataract is used to remove the lens. During the emulsification, emulsified particles of the natural lens are aspirated from the lens capsular bag and a balanced salt solution (BSS) is used to maintain the fluid inside the capsular bag and the intraocular pressure of the eye. Once the natural lens has been removed, it may be replaced by an artificial lens.

However, in some procedures the emulsified particles may not be completely aspirated, so that some remain inside the capsular bag. The remaining particles may be too small to be seen by the surgeon performing the procedure, and/or may be hidden, for example, by the iris of the eye being operated on. Any remaining emulsified particles compromise the vision provided by the artificial lens when it replaces the natural lens.

Embodiments of the present invention provide a flexible probe that has a camera at its distal end, and the distal end with the camera may be inserted into the capsular bag of an eye being operated on, after phacoemulsification has been performed. The probe is held at its proximal end by a handle, and the proximal end of the probe defines a symmetry axis. The distal end is highly bendable, being able to be controllably bent, in a first plane containing the symmetry axis, by angles up to 270°. The amount of bending of the distal end, herein termed the bending angle, is adjusted according to the position of a control in the handle.

An operator of the probe may use the handle to rotate the proximal end of the probe about the symmetry axis so that the bent distal end rotates, also in a controllable manner, in a second plane orthogonal to the axis and to the first plane. During the rotation the camera may be activated to acquire images internal to the eye, and the images may be presented on a screen, typically after stitching so as to provide a coherent image, for inspection by the operator.

By varying the bending angle of the distal end, and by rotating the distal end completely in the second plane, i.e., by 360°, for the different bending angles, the interior of the eye may be completely imaged. Any remaining emulsified particles are thus visible to the probe operator, and the operator may remove the particles before insertion of the artificial lens into the lens sack.

In one embodiment of the invention a magnetic field sensor is located at the distal end, and the sensor is configured to provide signals indicative of an orientation of the sensor, and thus of the bending angle in the first plane and of an angle of rotation in the second plane. The sensor operates in response to an alternating magnetic field transmitted to traverse the sensor.

In an alternative embodiment of the invention the bending angle in the first plane is provided by a look-up table relating the angle to a position of the control in the handle. In the alternative embodiment there is no magnetic field sensor at the distal end; rather, a magnetometer is fixed in the proximal end, and the magnetometer provides a signal indicative of an orientation of the magnetometer relative to a nonvarying local magnetic field, i.e., the Earth's magnetic field. The signal from the magnetometer is used to determine the angle of rotation in the second plane. By using a magnetometer, there is no need to provide an alternating magnetic field.

Elements of the flexible probe may be relatively low cost, and so the probe may be provided for one-time use, i.e., to be disposable.

DETAILED DESCRIPTION

Figure 1:
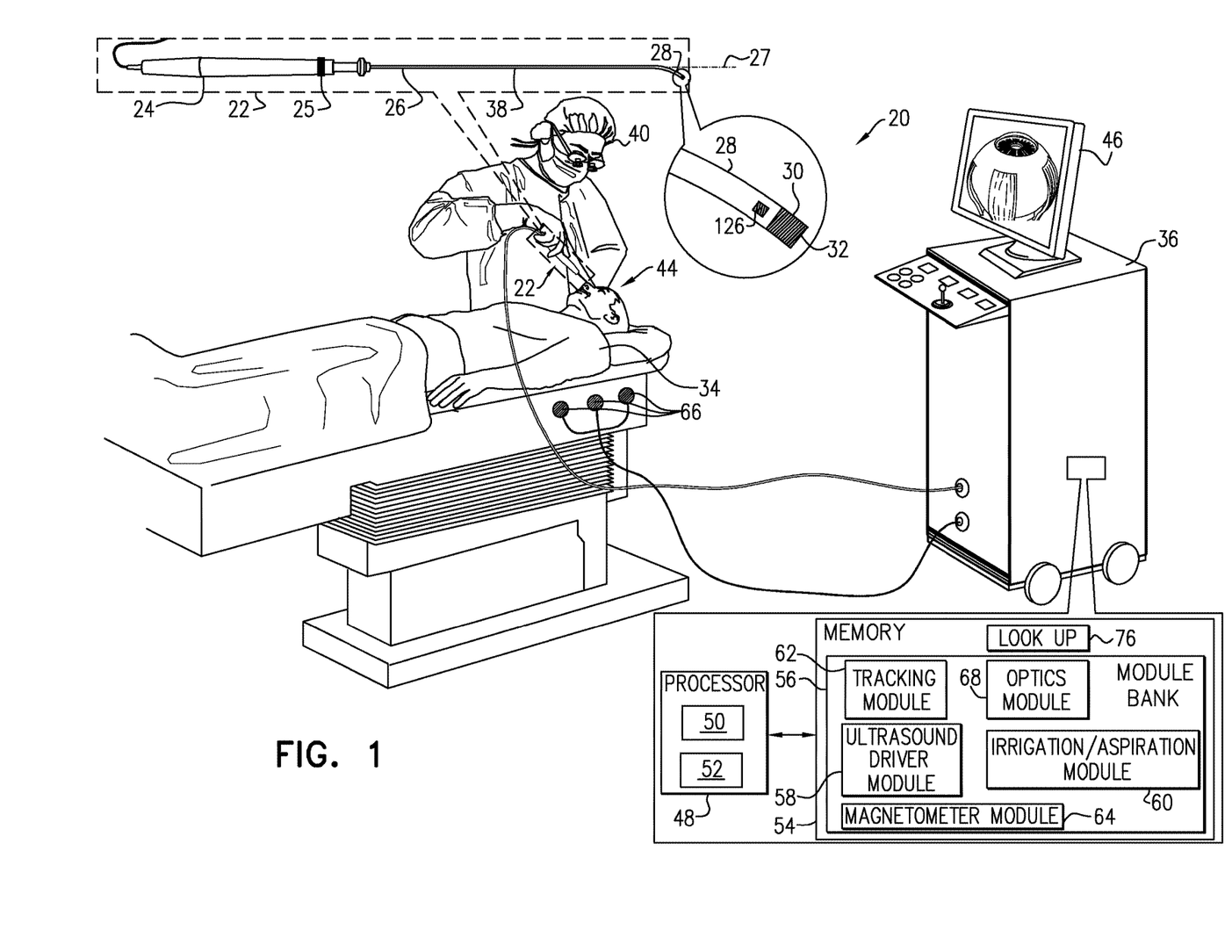
FIG. 1 is a schematic pictorial illustration of a medical system configured to be used when inspecting a phacoemulsification procedure, according to an embodiment of the present invention.

Reference is now made to FIG. 1, which is a schematic pictorial illustration of a medical system 20 configured to be used when inspecting a phacoemulsification procedure, according to an embodiment of the present invention. In the example shown in FIG. 1, medical system 20 comprises a camera probe 22 that is coupled to a control console 36. A medical professional 40 (also referred to herein as an operator) typically uses camera probe 22 during and after a phacoemulsification procedure performed by the operator on an eye 44 of a patient 34, so as to inspect the results of the procedure. In the following description, embodiments of probe 22 are differentiated, as necessary, by appending a letter to the identifying numeral 22.

Probe 22 has a handle 24, connected to a flexible tube 26. Flexible tube 26 comprises a manipulatable distal end 28, which in turn has a camera 30 fixedly attached to a distal tip 32 of the distal end. There is a proximal section 38 of tube 26 between distal end 28 and handle 24. Operator 40 holds handle 24, and is able to bend distal end 28 from a symmetry axis 27 of the unbent tube using a control 25 in the handle. Camera probe 22 is described in more detail with respect to FIGS. 2A, 2B, 2C and 2D below.

Control console 36 comprises a processor 48 which operates system 20. Processor 48 typically comprises real-time noise reduction circuitry 50 which may be configured as a field programmable gate array (FPGA), followed by an analog-to-digital (A/D) signal conversion integrated circuit 52. The processor can pass the signal from A/D circuit 52 to another processor and/or can be programmed to perform one or more algorithms disclosed herein, each of the one or more algorithms comprising steps described hereinbelow. In order to operate system 20, processor 48 is coupled to a memory 54, comprising a module bank 56 having a plurality of modules. Memory 54 may comprise any suitable volatile and/or non-volatile memory, such as random-access memory or a hard disk drive. Each of the modules may also typically comprising hardware elements, and the functionality of each of the modules is described below.

As stated above, system 20 may be used to inspect a phacoemulsification procedure, and the procedure may be performed using an ultrasonic probe. To operate the probe, processor 48 uses an ultrasound driver module 58 to provide driving signals at a pre-selected frequency, typically in a range between approximately 20 kHz and approximately 50 kHz, to the probe. The phacoemulsification procedure produces emulsified particles of the lens of eye 44, and the ultrasonic probe typically comprises irrigation and aspiration channels. Processor 48 uses an irrigation/aspiration module 60 to provide irrigation fluid, typically BSS, to the irrigation channel at a controlled rate. Simultaneously, the processor uses the irrigation/aspiration module to apply a controlled vacuum to the aspiration channel. The vacuum removes the emulsified particles of the lens and the irrigation fluid replaces the now-emulsified lens/fluid in the lens capsule. The processor uses module 60 to ensure that the irrigation and aspiration rates balance, so as not to cause trauma to the eye.

Typically, although not necessarily, the emulsification procedure and the inspection are performed serially, i.e., the inspection using system 20 is performed after the emulsification. FIG. 1 illustrates the inspection, and for simplicity the ultrasonic probe is not shown in the figure.

A disclosed embodiment of camera probe 22, herein referred to as probe 22A, is described in more detail below with respect to FIGS. 2A, 2B and 2C. In probe 22A processor 48 tracks the position, i.e., the three Cartesian coordinates of the location and the three mutually orthogonal angles of the orientation, of distal tip 32 of tube 26 of the probe using alternating magnetic fields traversing the probe. The processor uses a tracking module 62 to drive magnetic field transmitters 66, located in proximity to eye 44, so as to generate alternating magnetic fields at the eye. Probe 22A comprises a sensor 126 at the distal tip of the probe, and the sensor generates potential signals in response to the alternating fields traversing the sensor.

The potentials are fed back to module 62, and processor 48 uses the module to analyze the returning potentials so as to track the position of distal tip 32. Magnetic position tracking techniques such as are used here are described, for example, in U.S. Pat. Nos. 5,391,199, 5,443,489, 6,788,967, 5,558,091, 6,172,499 and 6,177,792. The techniques, including calibration of the magnetic transmitters and of sensors responding to the transmitters, are implemented in the CARTO® system, produced by Biosense Webster Inc. (33 Technology Drive, Irvine, California 92618 USA) and are described in detail in the patents cited above.

An alternative disclosed embodiment of probe 22, herein referred to as probe 22B, is described in more detail below with respect to FIG. 2D. In contrast to probe 22A, for probe 22B processor 48 tracks only two mutually orthogonal angles of orientation of distal tip 32. For probe 22B processor 48 does not track the location of the distal tip 32. In order to track one of the angles of orientation, a magnetometer, i.e., a sensor configured to measure a nonvarying magnetic field, is incorporated into a section of tube 26 proximate to distal end 28 of probe 22B, and the processor uses a magnetometer module 64 to read signal values of the local nonvarying magnetic field, i.e., the Earth's magnetic field, registered by the magnetometer as probe 22B is rotated about symmetry axis 27 of the probe. The processor uses the magnetometer signals to determine a first angle of orientation of distal tip 32 in a plane, herein also termed the symmetry plane, orthogonal to the symmetry axis.

An optics module 68 provides power and driving signals for camera 30, and imaging signals are generated by the camera 30 and return to the optics module 68. The signals are conveyed between the camera and the console by cabling connecting to the camera, via handle 24. Processor 48, together with the optics module 68, receives the imaging signals generated by the camera 30 and from the received signals provides an image of the scene viewed by the camera on a screen 46.

As stated above, operator 40 is able to bend distal end 28 using control 25 in handle 24. As explained below, distal end 28 bends in a plane containing symmetry axis 27 of probe 22, the plane, herein also termed the bending plane, being orthogonal to the symmetry plane. Control 25 is typically either a rotational or a linear device, and in an embodiment of the present invention an angle of bending of distal end 28 in the bending plane is calibrated against the position of the control.

Control 25 may be connected to a potentiometer, so that as the control 25 changes its position, a value generated by the potentiometer, such as a potential or a resistance, changes. The calibration, comprising a relation between the position of the control and the angle of bending caused by the control, may be stored, by way of example, as a bending angle look-up table 76 in memory 54, the look-up table having ordered pairs of potentiometer-generated values and bending angles. A second angle of orientation of distal tip 32 corresponds to the angle of bending of the distal end in the bending plane, and, from a given potentiometer-generated value, processor 48 determines the second angle using look-up table 76.

Figure 2A:
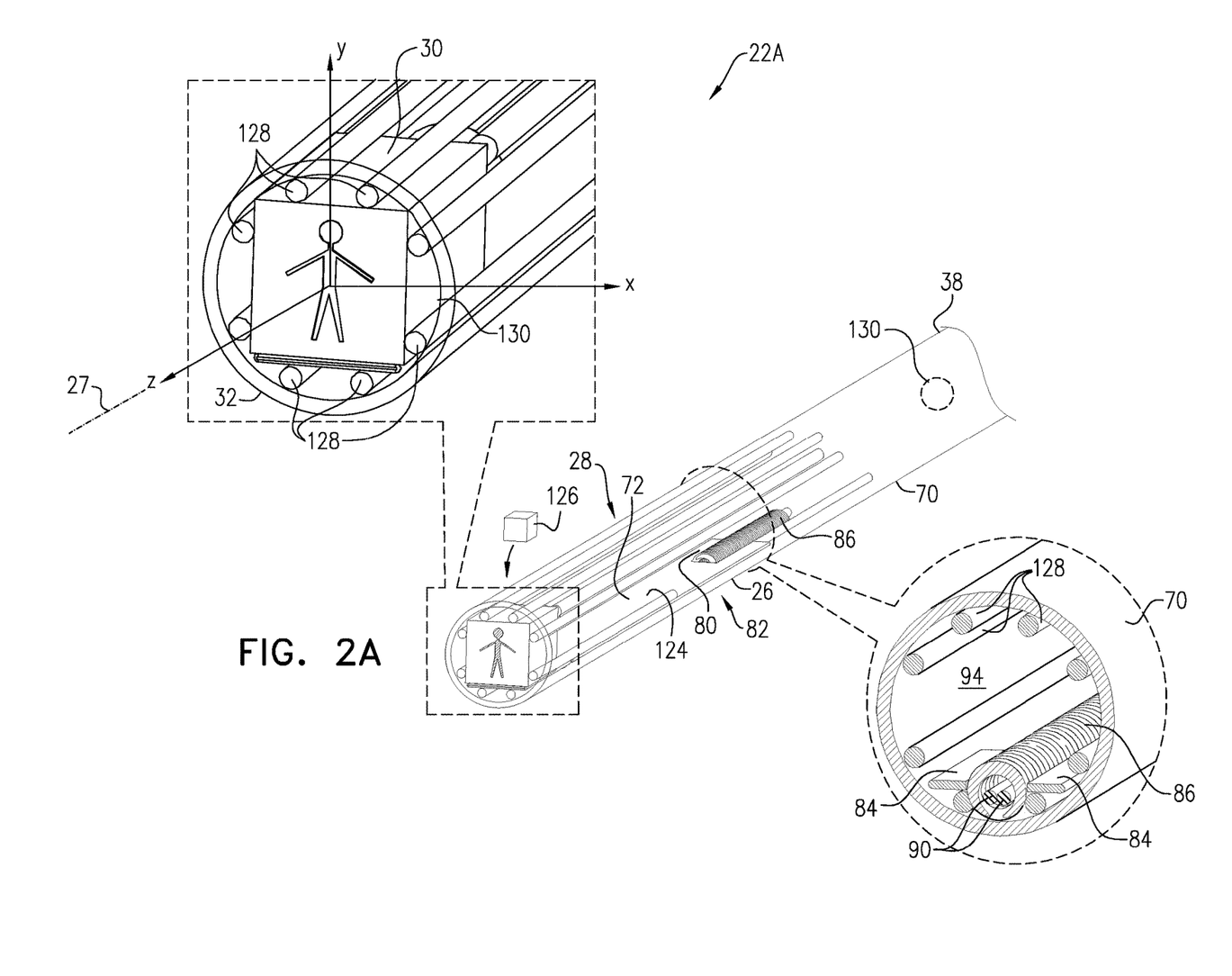
FIGS. 2A, 2B and 2C are schematic diagrams illustrating a tube of a probe used in the procedure, according to an embodiment of the present invention.
Figure 2B:
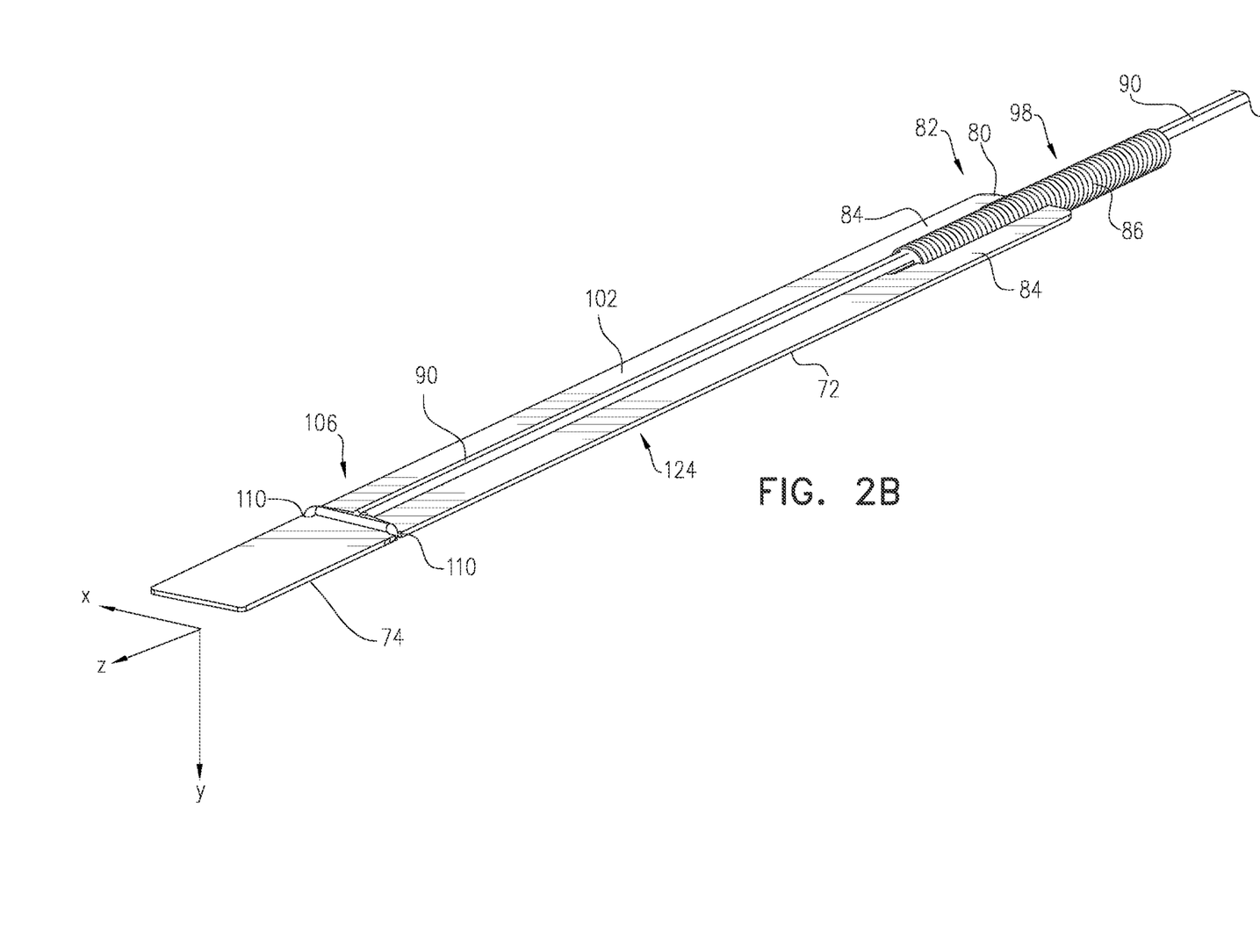
Figure 2C:
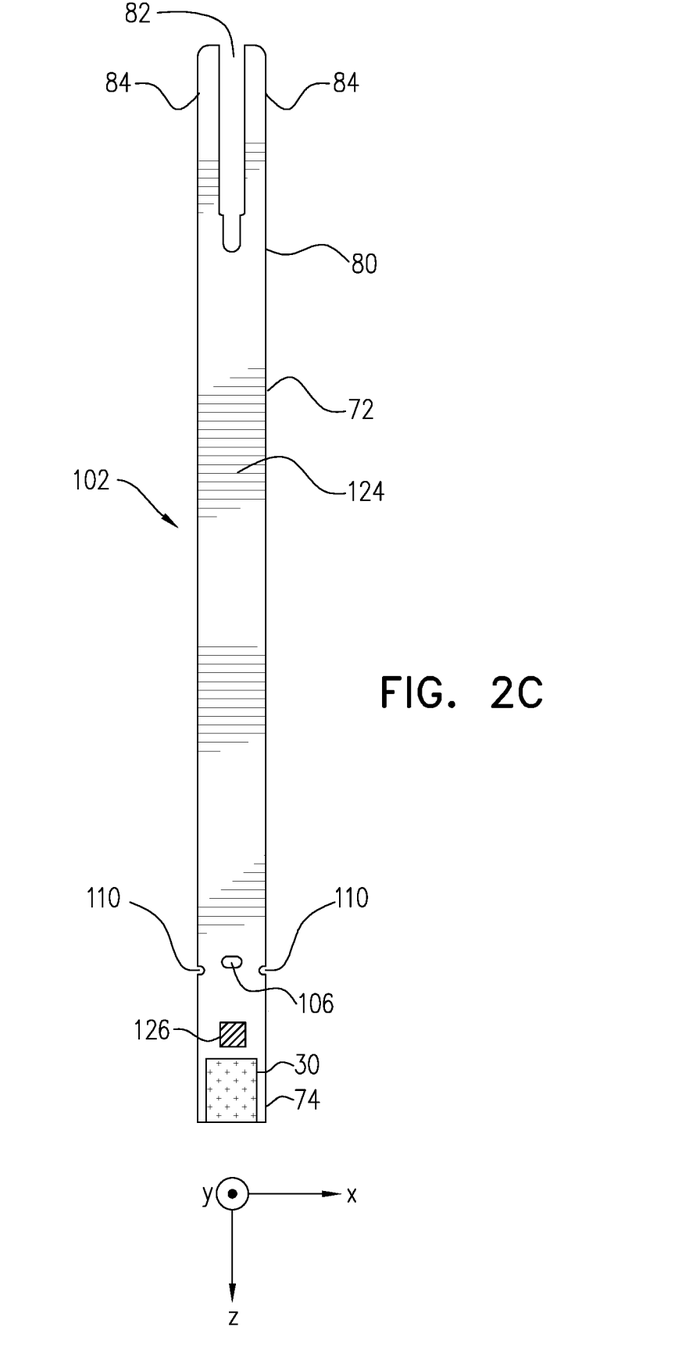

FIGS. 2A, 2B and 2C are schematic diagrams illustrating tube 26 of probe 22A, according to an embodiment of the present invention. FIG. 2A is a schematic perspective view of the tube 26, which comprises external biocompatible flexible tubing 70, typically formed from a plastic such as polyimide. Tubing 70 is shown as transparent in FIG. 2A. In one embodiment tubing 70 has an outer diameter suitable for insertion into an incision of the eye, e.g. 2.0 mm, and an inner diameter of 1.8 mm. The inner diameter is sized according to the components within tubing 70, and in other embodiments the inner diameter ranges between 1.4 mm and 3 mm, with the outer diameter varying respectively between 1.6 mm and 3.2 mm. FIGS. 2B and 2C illustrate elements internal to tubing 70. As stated above, camera 30 is fixedly attached to distal tip 32 of tube 26.

At distal end 28 of tube 26, inside tubing 70, there is a planar resilient strip 72. Strip 72 is typically formed from a super-elastic material such as nitinol, and is generally planar with a rectangular shape, except as described herein. In one embodiment, the strip 72 has dimensions with the following ranges: length 15-25 mm, width 1-1.5 mm, thickness 0.6-1.5 mm. Strip 72 is also referred to herein as insert 72.

In the following description, for clarity tube 26 is assumed to define a set of orthogonal xyz axes, where the z axis corresponds to axis of symmetry 27 of unbent tube 26, the x-axis is orthogonal to the z-axis so that insert 72 is in an xz plane, and the y-axis is orthogonal to the insert. FIG. 2A shows tube 26 viewed from above the xz plane; FIG. 2B, which has its xyz axes rotated about the z-axis by 180°, shows elements within the tube viewed from below the xz plane; FIG. 2C shows insert 72, viewed from above the xz plane.

Insert 72 comprises, at its proximal end 80, an opening 82 between two arms 84 formed in the insert. Opening 82 is configured to receive a coil spring 86, and when the coil is inserted into the opening, it is held in place by the elasticity of arms 84. Coil spring 86 is typically a tension spring, having coils contacting each other when the spring is unloaded. In one embodiment the spring has an outside diameter of 0.48 mm. On insertion, the spring is also held fixedly to arms 84 by glue and/or by welding, and the spring is positioned in the opening so that it is symmetrical with respect to insert 72, i.e., so that an axis of symmetry of the spring is coplanar with the insert.

A wire 90 is threaded from control 25 in handle 24, through a lumen 94 (shown in the sectional callout of FIG. 2A) contained in tubing 70, and through a central lumen 98 contained in spring 86. Control 25 is also referred to herein as wire control 25. As shown in FIGS. 2B and 2C, wire 90 traverses a lower surface 102 of insert 72 to an opening 106 at a distal end 74 of the insert. Wire 90 threads through opening 106, wraps round distal end 74 via indentations 110 in the distal end, and returns to the wire control of handle 24 by again traversing lower surface 102 and central lumen 98 of the coil spring. Thus, wire 90 is held by its two ends by the wire control in handle 24, and is fixed to distal end 74 of insert 72 at opening 106.

The wire control in handle 24 may be used to pull on wire 90, i.e., to exert a force on the two ends of the wire which are connected to the control. It will be understood that the force exerted by pulling wire 90 causes distal end 74 of the insert, and thus distal end 28 of tube 26, to bend downwards, i.e., in a direction defined by a vector from an upper surface 124 of the insert to a lower surface 102 of the insert.

The combination of coil spring 86 fixedly connected to planar resilient insert 72 enables distal end 28 to be deflected in a downward direction, while preventing the distal end from deflecting sideways. The combination also provides the distal end with sufficient rigidity so that, absent a pull from wire 90, it remains in an undeflected form, and returns to the undeflected form when any pull of the wire is released.

Figure 3:
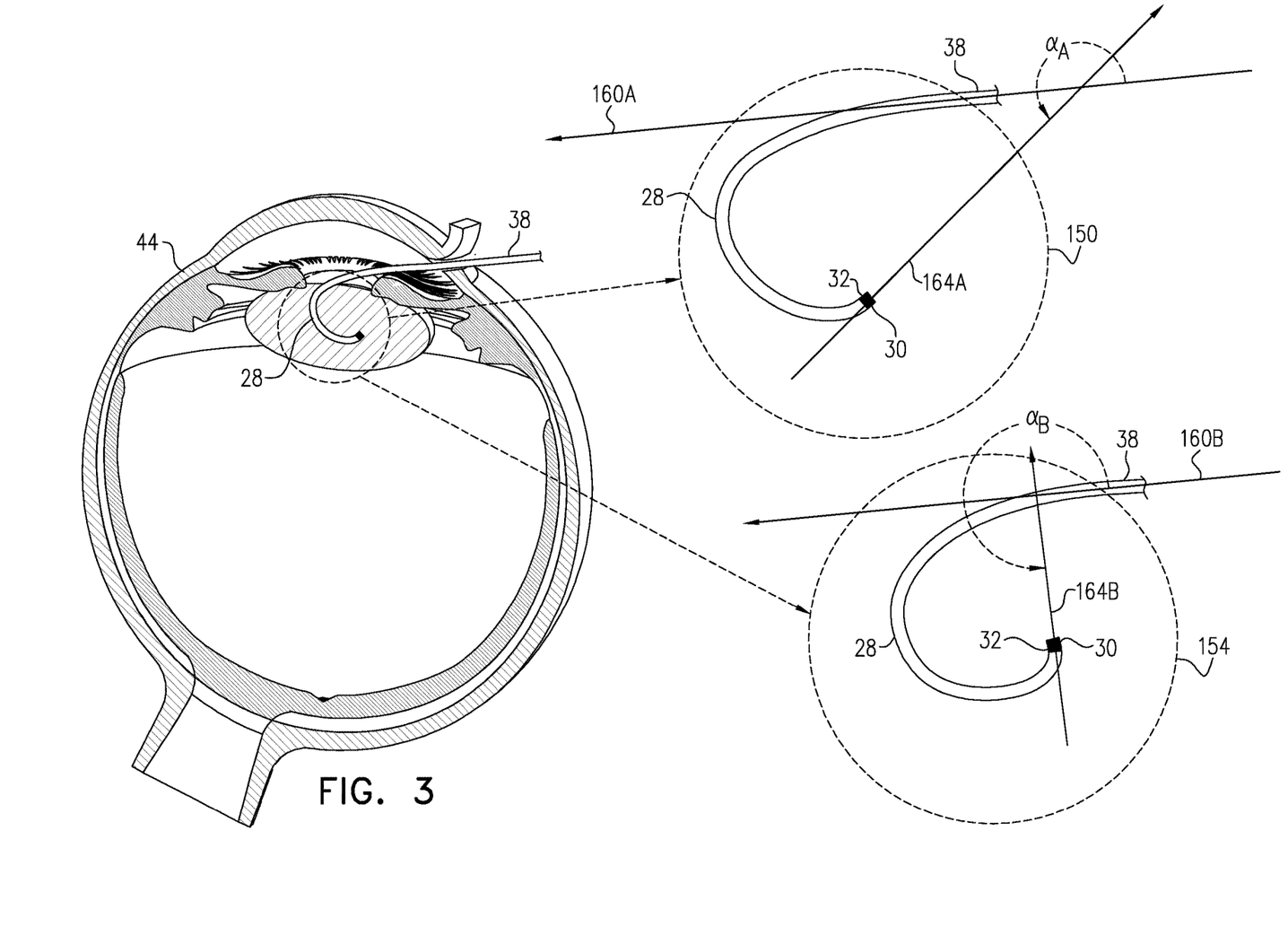
FIG. 3 is a schematic illustration of a probe inserted into an eye, according to an embodiment of the present invention.

While a single planar insert alone could provide the functionality described herein of the combination, the combination of the coil spring with the plane insert 72 significantly reduces the size needed for the insert, and thus of the tube, compared to that needed for the single insert alone. Furthermore, the lumen of the coil spring acts as a guide for wire 90, whereas if a single planar insert were used a guide providing the same functionality as the lumen of the spring would have to be made available. During bending, wire 90 is further constrained by tubing 70, so that in embodiments of the invention large bending angles are achievable with a small bending radius. In one embodiment of the present invention a bending angle of up to 270° for distal end 28, and a bending radius down to 1.5 mm for the distal end, are realized. FIG. 3 illustrates the bending angle of distal end 28.

FIGS. 2A and 2C illustrate the position of a magnetic field sensor 126, which is assumed to comprise a triple axis sensor (TAS) coil. Sensor 126 is mounted, by gluing, onto upper surface 124 at the distal end 74 of insert 72. The alternating magnetic fields from transmitters 66 generate potentials in sensor 126, and, as stated above, the potential signals are fed back via handle 24 to module 62. Processor 48 uses module 62 to analyze the signals, and from the analysis determines a position, i.e., a location and an orientation, of distal tip 32.

Other arrangements for determining the position of distal tip 32 are assumed to be comprised within the scope of the present invention. Such arrangements include, but are not limited to:
 a single axis sensor (SAS) at distal end 74 of strip 72, in place of sensor 126, and a double axis sensor (DAS) at a location 130 in proximal section 38;
 a first SAS at distal end 74 of strip 72, in place of sensor 126, and a second SAS, orthogonal to the first SAS, at location 130 in proximal section 38;
 a magnetometer at distal end 74 of strip 72, in place of sensor 126; and
 a DAS or a TAS at location 130 in proximal section 38, and a control such as control 25 setting the bending angle of distal end 28.

For clarity, except where otherwise stated, the description herein assumes that processor 48 determines the position of distal tip 32 from signals generated by sensor 126. Those having ordinary skill in the art will be able to adapt the description, *mutatis mutandis*, for the other arrangements provided above.

Camera 30 is also fixedly mounted on upper surface 124 at the distal end of insert 72, i.e., at distal tip 32, so that the position of the distal tip found by processor 48 is also the position of the camera. Illumination for camera 30 is provided in probe 22 via fiber optics 128, located in lumen 94 and having distal terminations at distal tip 32. The illumination is provided by one or more LEDs (light emitting diodes), not shown in the figures, coupled to proximal terminations of the fiber optics.

Figure 2D:
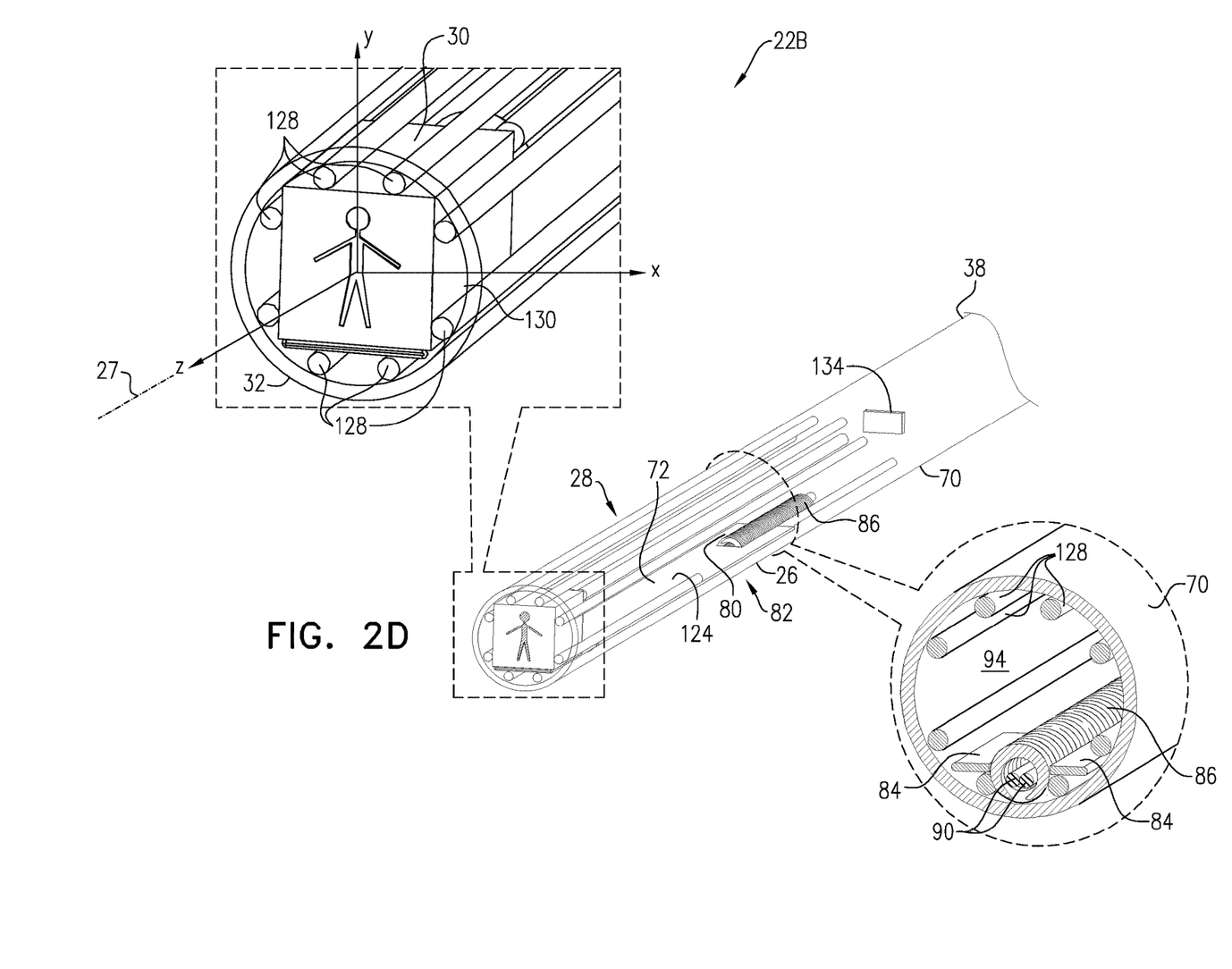
FIG. 2D is a schematic diagram illustrating a tube of a probe used in the procedure, according to an alternative embodiment of the present invention.

FIG. 2D is a schematic diagram illustrating tube 26 of probe 22B, according to an alternative embodiment of the present invention. Apart from the differences described below, the operation of probe 22B is generally similar to that of probe 22A (FIGS. 2A, 2B and 2C), and elements indicated by the same reference numerals in both probes 22A and 22B are generally similar in construction and in operation.

In contrast to probe 22A, probe 22B does not have sensor 126 at the distal end of insert 72. In place of sensor 126, a magnetometer 134 is fixed within lumen 94, in proximal section 38 of the tube 26, i.e., proximal to distal end 28. Thus, when distal end 28 bends, due to wire 90 being pulled, magnetometer 134 does not move. This is in contrast to sensor 126 of probe 22A, which does move when distal end 28 bends.

Magnetometer module 64 provides power to magnetometer 134, and, as stated above, receives signals from the magnetometer generated in response to the local nonvarying magnetic field traversing the magnetometer. Processor 48 analyzes the received signals to formulate an indication of the orientation of the magnetometer, and thus an indication of the orientation of proximal section 38, in a direction orthogonal to symmetry axis 27.

While magnetometer 134 may be configured to provide its orientation absolutely, i.e., with respect to magnetic North, embodiments of the present invention typically do not require this. Rather, as is explained in the description of the flowchart of FIG. 4, embodiments of the present invention use the magnetometer to provide a relative orientation measured with respect to an arbitrary orientation.

As stated above, control 25 bends distal end 28, and processor 48 is able to access look-up table 76, for a given position of the control, i.e., for a given potentiometer-generated value determined by the processor, to find the angle of bending of the distal end. It will be understood that the orientation of proximal section 38 provided by the magnetometer, taken together with the angle of bending from the look-up table, enables processor 48 to formulate an orientation for camera 30.

FIG. 3 is a schematic illustration of probe 22 inserted into eye 44, according to an embodiment of the present invention. The figure illustrates distal end 28 within a capsular bag of the eye, after the lens of the eye has been emulsified and aspirated, and when the capsular bag is filled with BSS and/or viscoelastic. Distal end 28 is assumed to have been bent using control 25. A first callout 150 illustrates one bending of the distal end, and a second callout 154 illustrates a second bending of the distal end.

In the disclosure and in the claims, a bending angle α of distal end 28 is defined as the angle between a first directed line segment 160, collinear with and extending distally from proximal section 38, and a second directed line segment 164 collinear with and extending distally from a local z-axis of the distal tip. Bending angles and their defining line segments are differentiated, as necessary, by appending, or adding as a subscript, a letter to the angle or line segment identifier. Thus, callout 150 illustrates bending angle αA as being defined by first line segment 160A and second line segment 164A, and callout 154 illustrates bending angle αB as being defined by first line segment 160B and second line segment 164B.

Prior to the insertion illustrated in FIG. 3, bending angle look-up table 76 for a given probe 22 may be formulated in a calibration process. In the process, the proximal end of the probe is fixed and mounted so that the distal end, with camera 30, points to a fixed screen. The camera then acquires respective images of the screen with the probe distal end undeflected, as well as for the distal end deflected by different preset positions of control 25. For each image processor 48 records the preset position of control 25. The processor also determines the directed line segment, and thus the value of bending angle α for each preset position of the control. The processor inserts the pairs of values of the preset positions and the bending angles into the look-up table.

Once formulated, the results of the look-up table may be presented on screen 46 (as is described with reference to FIG. 5 below) so that operator 40 may see the bending angle formed for a given position of control 25.

As stated above, the inventors have found that bending angle α may have a value up to 270°. It will be understood that such a large bending angle is enabled because the combination of the lumen of spring 86, insert 72, and the lumen of tubing 70 all restrain wire 90 so as to redirect the direction of the force applied by the wire.

The inventors have also found that a local radius of curvature of distal end 28, typically at distal tip 32, can be as low as 1.5 mm.

Figure 4:
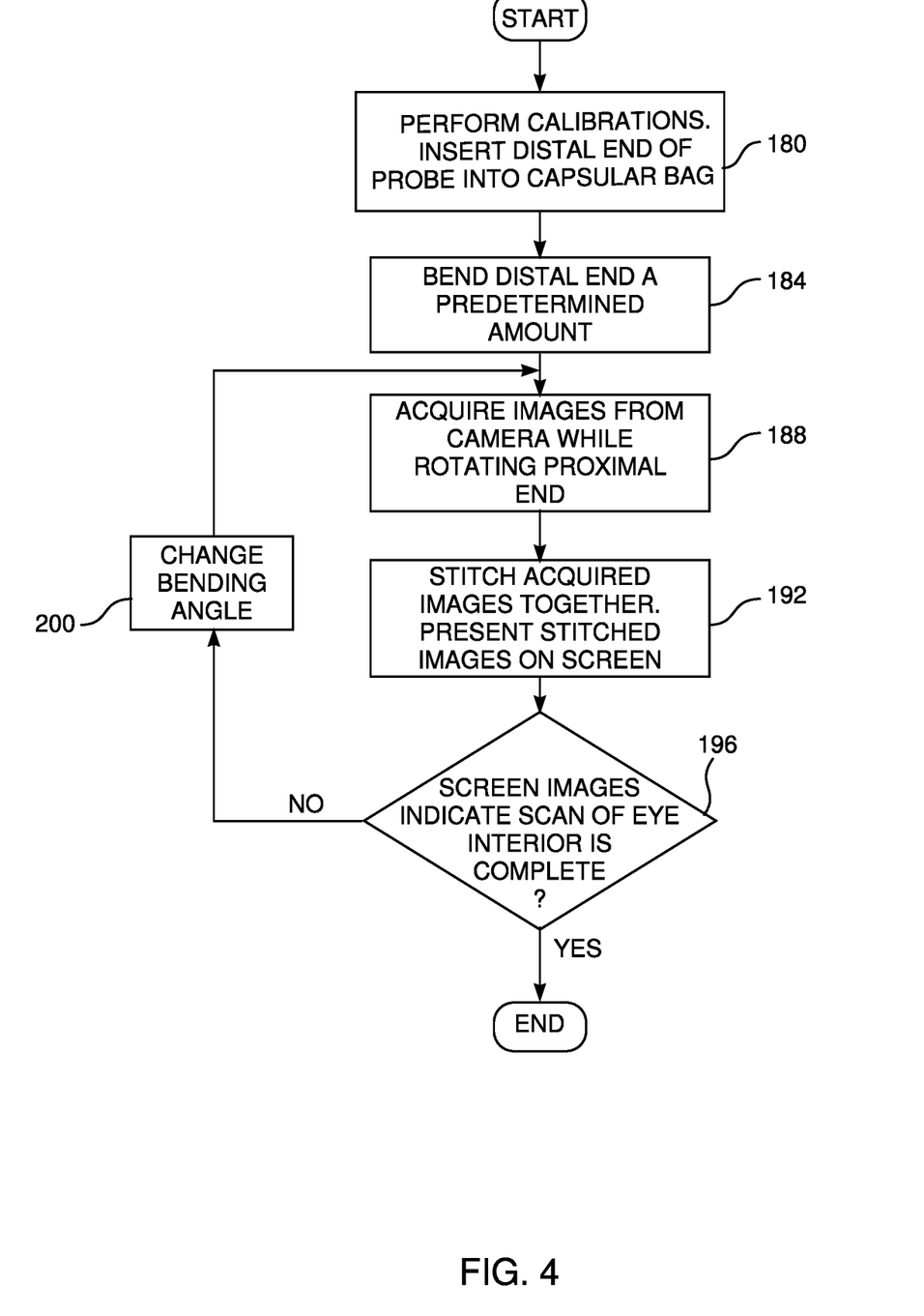
FIG. 4 is a flowchart of steps of a procedure for inspecting results of a phacoemulsification of an eye lens, according to an embodiment of the present invention.
Figure 5:
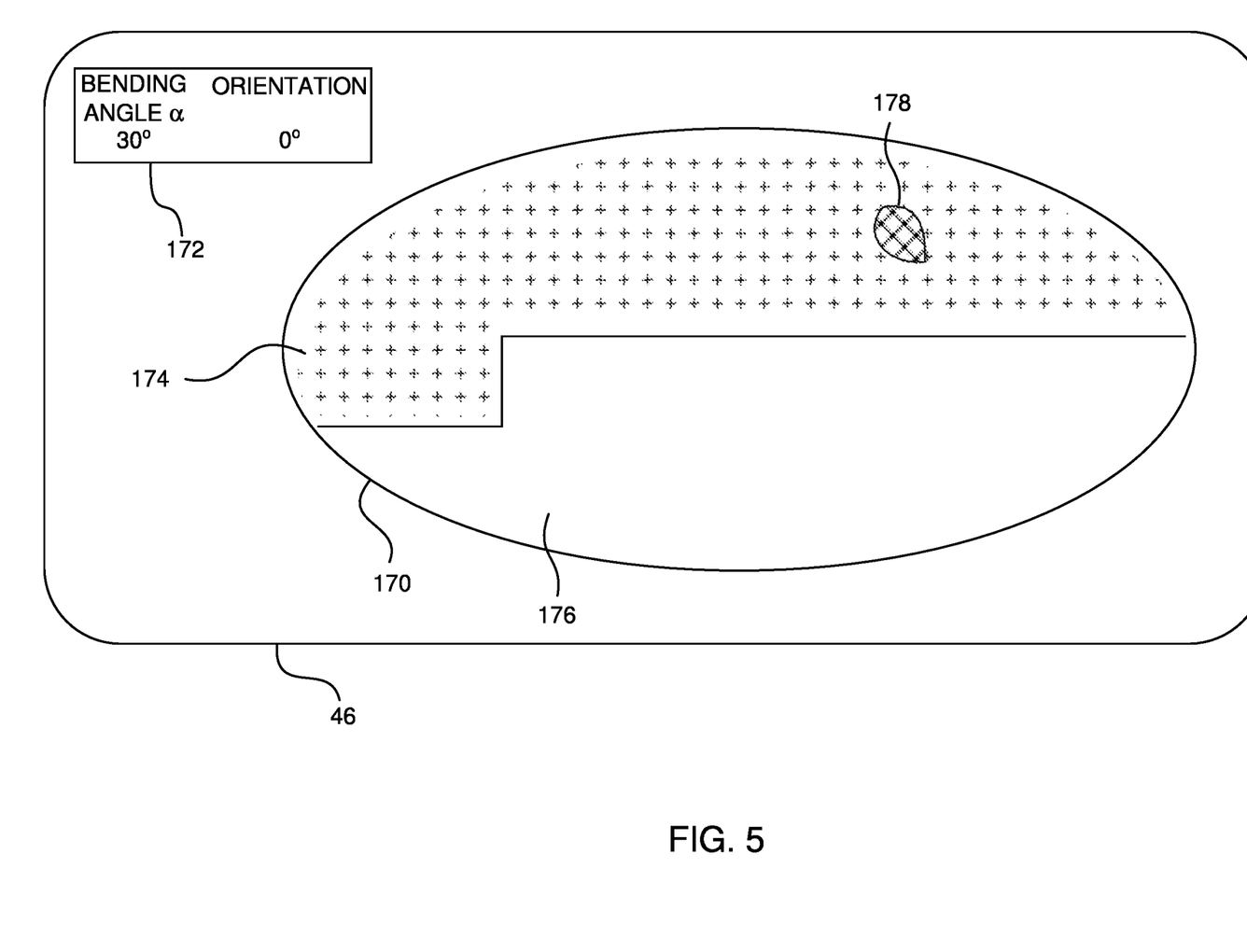
FIG. 5 is a schematic diagram of a screen used during the inspection procedure, according to an embodiment of the present invention.

FIG. 4 is a flowchart of steps of a procedure for inspecting results of a phacoemulsification of an eye lens, and FIG. 5 is a schematic diagram of a screen used during the procedure, according to an embodiment of the present invention. The inspection generates a three-dimensional (3D) image of the interior of eye 44, and the 3D image, or portions of it, are projected as two-dimensional (2D) images in the interior of an ellipse 170 formed on screen 36. Screen 36 also has a notification region 172, presenting a value of the bending angle α of the distal end 28 of the probe 20, determined from look-up table 76, as it is used during the inspection. Region 172 is also used to present a value of the orientation of the distal end 28 of the probe. The orientation value presented is described further below.

In an initial step 180, if the procedure uses probe 22A, then processor 48 performs a calibration of transmitters 66 and sensor 126, as referred to above in the description of FIG. 1, so as to track distal end 28.

Alternatively, if the procedure uses probe 22B, then the processor 48 performs a calibration of the probe so as to generate look-up table 76, as described above with reference to FIG. 3. In the remainder of the description of the flowchart it is assumed that probe 22B is used, and those having ordinary skill in the art will be able to adapt the description, *mutatis mutandis*, if probe 22A is used.

Once the calibration referred to above has been performed, and after the lens of eye 44 has been emulsified and has been replaced by BSS and/or viscoelastic, operator 40 inserts distal end 28 of the probe into the capsular bag of the eye.

In a bending step 184, the operator uses control 25 and notification region 172 to bend the probe 20 distal end 28 by a preset amount, for example 30°.

In an image acquisition step 188, the operator activates camera 30 to acquire images of internal portions of eye 44, and rotates the proximal section of probe 22 as the images are being acquired. Prior to beginning the rotation, the operator activates magnetometer 134 and processor 48 applies the signals from the magnetometer to record an initial, arbitrary, orientation, in the symmetry plane, of the distal end 28. Processor 48 may confirm the activation to the operator 40 by setting a value of the orientation in region 172 to 0°.

As the proximal section is rotated, processor 48 together with magnetometer module 64 uses the change of signals from the magnetometer, i.e., the difference in the magnetometer signals from the initial signals, to calculate a relative orientation of the magnetometer with respect to the initial orientation. It will be understood that the magnetometer relative orientation is also the relative orientation of the distal end 28 and of the camera 30. The relative orientation is displayed in region 172, and the operator 40 continues to rotate the proximal section 38 until the orientation again displays as the initial orientation value 0°, showing that the distal end 28 has performed a complete rotation of 360°.

For each image acquired, processor 48 stores the image together with the relative orientation and the bending angle of the distal end 28.

In an image display step 192, processor 48 stitches the images acquired during the rotation of step 188, using common image elements such as blood vessels and sections of the retina, as well as the recorded values of the relative orientations. A method for stitching is described in an article by S. Mann and R. W. Picard, titled "Virtual bellows: constructing high quality stills from video," (Proceedings of 1st International Conference on Image Processing, Austin, TX, 1994, pp. 363-367 vol. 1). The method described therein, or any other convenient stitching method known in the art, may be used in step 192. The stitching generates a unified composite coherent image of a three-dimensional (3D) slice imaged by camera 30, and processor 48 presents a 2D projection of the 3D image within ellipse 170. #

As shown by a decision step 196, and a change bending angle step 200, steps 188 and 192 are iterated, for different values of bending angle α. The iterations continue until the interior of ellipse 170 is filled, indicating that the interior of eye 44 has been completely scanned and imaged, at which point the flowchart terminates.

FIG. 5 has been drawn to illustrate partial scanning of the interior of eye 44. A region 174 has 2D stitched images from steps 188 and 192; a region 176 indicates a part of the interior of the eye that has not been scanned or imaged.

Once the scanning described by the flowchart terminates, or during the scanning, operator 40 may inspect the 2D images in the interior of ellipse 170 and check for the existence of emulsified lens particles. Such a particle is illustrated in FIG. 5 by an irregular oval 178. If such a particle is observed, the operator may reintroduce the phacoemulsification probe into the capsular bag and aspirate the particle.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising:
a camera probe for use in eye surgeries, the camera probe comprising:
    a flexible biocompatible tube, comprising a proximal end, a distal end, and an internal lumen, wherein the distal end is configured to bend by up to 270°, and wherein the tube is configured and dimensioned to be inserted into a lens capsular bag of an eye;
    a planar resilient strip, comprising a proximal end and a distal end, wherein the strip is inserted into the internal lumen, and wherein the distal end of the strip is fixed to the distal end of the tube;
    a coil spring, comprising a lumen, wherein the coil spring is fixed to the proximal end of the strip so that an axis of symmetry of the coil spring is coplanar with the strip;
    a camera mounted with the distal end of the strip;
    a wire, extending through the lumen of the coil spring and having a termination fixed to the distal end of the strip, so that a predetermined force on the wire causes the distal end of the tube to bend by a preset bending angle of up to 270°; and
    a magnetometer mounted within the internal lumen at the proximal end of the tube, and configured, in response to a nonvarying magnetic field traversing the magnetometer, to provide a signal that, when taken with the preset bending angle, is indicative of an orientation of the camera within the eye when a proximal end of the tube is turned, wherein the camera is configured to image an internal portion of the eye using the preset bending angle and rotating the proximal end of the tube 360° about a symmetry axis of the proximal end of the tube based on the signal.

2. The apparatus according to claim 1, further comprising a handle, connected to the proximal end of the tube, wherein the handle comprises a control configured to apply the predetermined force on the wire.

3. The apparatus according to claim 1, wherein the signal provided by the magnetometer comprises a difference between an initial signal, generated when the orientation of the camera is in an initial orientation, and a subsequent signal, generated when the orientation of the camera is in a subsequent orientation different from the initial orientation.

4. The apparatus according to claim 1, wherein the coil spring comprises a tension spring having coils contacting each other when the coil spring is unloaded.

5. The apparatus according to claim 1, further comprising at least one fiber optic located in the internal lumen and configured to provide illumination to the internal portion of the eye imaged by the camera.

6. A method, comprising:
providing an apparatus, comprising:
    a flexible biocompatible tube having a proximal end, a distal end, an internal lumen, wherein the distal end is configured to bend by up to 270°; a magnetometer, wherein the magnetometer is coupled with the internal lumen at the proximal end of the tube, and wherein the magnetometer is configured to provide a signal indicative of an orientation of the magnetometer with respect to a nonvarying magnetic field traversing the magnetometer; and a camera, wherein the camera is coupled with the distal end of the tube;
inserting the distal end of the tube into an eye;
bending the distal end of the tube by a preset bending angle;
rotating the proximal end of the tube about a symmetry axis of the proximal end, while activating the camera to acquire images of an internal portion of the eye;
in response to the signal provided by the magnetometer, halting rotation of the proximal end when the rotation is 360°; and
presenting the images acquired by the camera during the rotation on a screen.

7. The method according to claim 6, wherein presenting the images comprises stitching the images to form a coherent image of the internal portion of the eye.

8. The method according to claim 6, further comprising performing an iteration of the steps of bending the distal end of the tube, rotating the proximal end of the tube, and halting rotation of the proximal end when the rotation is 360°, and wherein presenting the images comprises presenting the images acquired during the iteration.

9. The method according to claim 8, further comprising halting the iteration when the internal portion of the eye has been completely imaged.

10. An eye imaging apparatus comprising:
    a flexible biocompatible tube, comprising an internal lumen having a proximal end and a distal end, wherein the distal end of the tube is configured to bend by up to 270°, and wherein the tube is configured and dimensioned to be inserted into a capsular bag of an eye;
    a planar resilient strip, comprising a proximal end and a distal end, wherein the strip is inserted into the internal lumen, and the distal end of the strip is fixed to the distal end of the tube;
    a coil spring, comprising a coil lumen, wherein the coil spring is fixed to the proximal end of the strip so that an axis of symmetry of the coil spring is coplanar with the strip;
    a camera mounted at the distal end of the strip;
    a wire, extending through the coil lumen and having a termination fixed to the distal end of the strip, so that a force on the wire causes the distal end of the tube to bend in the first plane by up to 270°; and
    a magnetic field sensor mounted with the distal end of the strip, and configured, in response to a magnetic field traversing the sensor, to provide a signal that is indicative of an orientation of the camera within the eye as the proximal end of the tube is rotated and the distal end of the tube is bent at a preset bending angle, wherein the camera is configured to image an internal portion of the eye using the preset bending angle and rotating the proximal end of the tube 360° about a symmetry axis of the proximal end of the tube based on the signal.

11. The apparatus according to claim 10, wherein the coil spring comprises a tension spring having coils contacting each other when the spring is unloaded.

12. The apparatus according to claim 1, further comprising at least one fiber optic located in the internal lumen and configured to provide illumination to the internal portion imaged by the camera.

13. The apparatus of claim 1, further comprising:
the control console communicatively coupled to the camera probe, the control console including a processor to analyze and determine the orientation of the camera based on the signal from the magnetometer and the preset angle.

* * * * *